(12) United States Patent
Fedorov et al.

(10) Patent No.: US 8,690,886 B2
(45) Date of Patent: Apr. 8, 2014

(54) POSTERIOR INSERTION INSTRUMENT FOR AN EXPANDABLE SUPPORT DEVICE

(75) Inventors: Sergey A. Fedorov, The Colony, TX (US); Nelson Li, Hillsdale, NJ (US)

(73) Assignee: Blackston Medical, Inc., Lewisville, TX (US)

( * ) Notice: Subject to any disclaimer, the term of this patent is extended or adjusted under 35 U.S.C. 154(b) by 69 days.

(21) Appl. No.: 13/174,731

(22) Filed: Jun. 30, 2011

(65) Prior Publication Data

US 2013/0006359 A1   Jan. 3, 2013

(51) Int. Cl.
  *A61B 17/88*   (2006.01)
  *A61F 2/44*   (2006.01)

(52) U.S. Cl.
  USPC .................. 606/99; 623/17.15; 623/17.16

(58) Field of Classification Search
  CPC .................................................... A61F 2/4637
  USPC ............. 606/99, 100, 914; 623/17.15–17.16, 623/911, 923
  See application file for complete search history.

(56) References Cited

U.S. PATENT DOCUMENTS

| | | | |
|---|---|---|---|
| 3,984,191 | A | 10/1976 | Doty |
| 5,611,639 | A | 3/1997 | Levenberg |
| 5,704,100 | A | 1/1998 | Swan |
| 6,176,881 | B1 | 1/2001 | Schar et al. |
| 6,644,884 | B2 | 11/2003 | Gledhill |
| 6,743,463 | B2 | 6/2004 | Weber et al. |
| 6,861,088 | B2 | 3/2005 | Weber et al. |
| 7,156,874 | B2 | 1/2007 | Paponneau et al. |
| 7,278,185 | B2 | 10/2007 | Smith |
| 7,455,875 | B2 | 11/2008 | Weber et al. |
| 7,588,573 | B2 * | 9/2009 | Berry ........................ 606/86 A |
| 7,914,581 | B2 | 3/2011 | Dickson et al. |
| 8,252,054 | B2 | 8/2012 | Greenhalgh et al. |
| 2006/0004376 | A1 | 1/2006 | Shipp et al. |
| 2006/0004447 | A1 | 1/2006 | Mastrorio et al. |
| 2006/0069436 | A1 | 3/2006 | Sutton et al. |
| 2007/0191954 | A1 * | 8/2007 | Hansell et al. ............. 623/17.15 |
| 2009/0138089 | A1 | 5/2009 | Doubler et al. |

(Continued)

FOREIGN PATENT DOCUMENTS

WO   03082363 A1   11/2003

OTHER PUBLICATIONS

International Search Report and Written Opinion; PCT/US2012/044959, dated Sep. 25, 2012, 7 pages.

(Continued)

*Primary Examiner* — Eduardo C Robert
*Assistant Examiner* — Julianna N Harvey
(74) *Attorney, Agent, or Firm* — Baker & McKenzie LLP (57) ABSTRACT

An insertion instrument for inserting an expandable support device, where the insertion instrument includes an actuator device operable to rotate a component of an expandable support device to a rotated position, such that the rotation to the rotated position of the expandable support device causes a first longitudinally extending member of the expandable support device to be longitudinally fixed. The insertion instrument also includes a hollow body, where the hollow body includes a removable gear device or a removable screw driver device. The removable gear device is configurable to cause a first longitudinally extending member of expandable support device to longitudinally extend in a direction away from the center of the expandable support device. The removable screw driver device is configurable to insert a screw into the expandable support device to lock the rotated position into place.

20 Claims, 9 Drawing Sheets

(56) References Cited

U.S. PATENT DOCUMENTS

| | | | |
|---|---|---|---|
| 2009/0204215 A1* | 8/2009 | McClintock et al. | 623/17.11 |
| 2009/0281579 A1 | 11/2009 | Weaver et al. | |
| 2010/0145456 A1 | 6/2010 | Simpson et al. | |
| 2010/0179657 A1 | 7/2010 | Greenhalgh et al. | |
| 2010/0274357 A1 | 10/2010 | Miller et al. | |
| 2010/0298942 A1 | 11/2010 | Hansell et al. | |
| 2011/0112587 A1 | 5/2011 | Patel et al. | |
| 2011/0251692 A1* | 10/2011 | McLaughlin et al. | 623/17.16 |

OTHER PUBLICATIONS

International Search Report and Written Opinion; PCT/US2012/044963, dated Sep. 25, 2012, 6 pages.

Walton, et al., "Inhibition of Prostaglandin E2 Synthesis in Abdominal Aortic Aneurysms: Implications for Smooth Muscle Cell Viability, Inflammatory Processes, and the Expansion of Abdominal Aortic Aneurysms," Circulation Jul. 6, 1999, pp. 48-54.

Tambiah, et al., "Provocation of experimental aortic inflammation and dilatation by inflammatory mediators and *Chlamydia pneumoniae*," British Journal of Surgery, 2001, 88, pp. 935-940.

Franklin, et al., "Uptake of tetracycline by aortic aneurysm wall and its effect on inflammation and proteolysis," British Journal of Surgery, 1999, 86, pp. 771-775.

Xu, et al., "Sp1 Increases Expression of Cyclooxygenase-2 in Hypoxic Vascular Endothelium: Implications for the Mechanisms of Aortic Aneurysm and Heart Failure," The Journal of Biological Chemistry, vol. 275, No. 32, Issue Aug. 11 2000, pp. 24583-24589.

Pyo, et al., "Targeted gene disruption of matrix metalloproteinase-9 (gelatinase B) suppresses development of experimental abdominal aortic aneurysms," The Journal of Clinical Investigation, Jun. 2000, vol. 105, No. 11, pp. 1641-1649.

\* cited by examiner

POSTERIOR INSERTION INSTRUMENT FOR AN EXPANDABLE SUPPORT DEVICE

TECHNICAL FIELD

The present disclosure relates in general to medical device technology, and more specifically to a posterior insertion instrument for an expandable support device.

BACKGROUND

Generally, a vertebral body replacement is inserted through an anterior incision, which is an invasive surgery requiring many tools. Typically, many organs and blood vessels must be maneuvered and disturbed to insert the vertebral body replacement between vertebral bodies. Further, physicians may be required to make another posterior incision to insert rods and pins to effectively lock the vertebral body replacement into place. Thus, many different tools may be required to insert, place, and lock vertebral body replacement into its desired position. Additional tools are typically required to manipulate expandable vertebral body replacements.

There remains a need for a multifunctional insertion instrument that can perform all of the requirements to insert, place, expand, and lock an expandable vertebral body replacement. Further, there remains a need for using an insertion instrument in a posterior procedure, which is less invasive than an anterior procedure, to place a vertebral body replacement by insertion between nerve roots and behind the spinal cord.

SUMMARY

In accordance with the present disclosure, an insertion instrument is provided for inserting an expandable support device, where the insertion instrument includes an actuator device operable to rotate a component of an expandable support device to a rotated position, such that the rotation to the rotated position of the expandable support device causes a first longitudinally extending member of the expandable support device to be longitudinally fixed. The insertion instrument also includes a hollow body, where the hollow body includes a removable gear device or a removable screw driver device. The removable gear device is configurable to cause a first longitudinally extending member of expandable support device to longitudinally extend in a direction away from the center of the expandable support device. The removable screw driver device is configurable to insert a screw into the expandable support device to lock the rotated position into place.

In accordance with the present disclosure, a method is provided for inserting an expandable support device with an insertion instrument, by securing an expandable support device to an insertion instrument, such that the insertion instrument includes a removable gear device and an actuator device. The method further includes positioning the expandable support device in a longitudinal position between vertebral bodies and interacting with the removable gear device to cause a first longitudinally extending member of the expandable support device to longitudinally extend in a direction away from the center of the expandable support device. The method further includes interacting with the actuator device to rotate a component of the expandable support device to a rotated position, where the rotation to the rotated position of the expandable support device causes the first longitudinally extending member of the expandable support device to be longitudinally fixed. The method further includes removing the removable gear device from a cannulation of the insertion instrument and inserting a removable screw driver device into the cannulation of the insertion instrument. The method further includes interacting with the removable screw driver device to insert a screw into the expandable support device to lock the rotated position into place.

The present disclosure provides several important technical advantages. In certain embodiments, the present disclosure provides a multifunctional instrument that can perform all of the requirements to insert, place, expand, and lock an expandable vertebral body replacement. Further, the present disclosure provides for using an insertion instrument in a posterior procedure, which is less invasive than an anterior procedure, to place a vertebral body replacement by insertion between nerve roots and behind the spinal cord. Accordingly, a patient's surgery time and recovery time may be dramatically reduced.

Other technical advantages of the present disclosure will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the features and advantages of the present disclosure, reference is now made to the detailed description along with the accompanying figures and in which.

DETAILED DESCRIPTION

While the making and using of various embodiments of the insertion instrument 100 according to the present disclosure are discussed in detail below, it should be appreciated that the present application provides many applicable inventive concepts that can be embodied in a wide variety of specific contexts. Without limiting the scope of the present disclosure, the insertion instrument 100 is described in connection with an expandable support device 4 having an upper extension leg and a lower extension leg. However, insertion instrument 100 can be used with other devices (e.g., expandable support devices which only has one extension leg, etc.). In some embodiments, the insertion instrument 100 described herein may used as a posterior insertion instrument 100. However, insertion instrument 100 may be used in posterior, anterior, anterolateral, or posterolateral procedures. The specific embodiments discussed herein are merely illustrative of specific ways to make and use the posterior insertion instrument disclosed herein and do not delimit the scope of the application, and their usage does not delimit the application, except as outlined in the claims.

Figure 1:
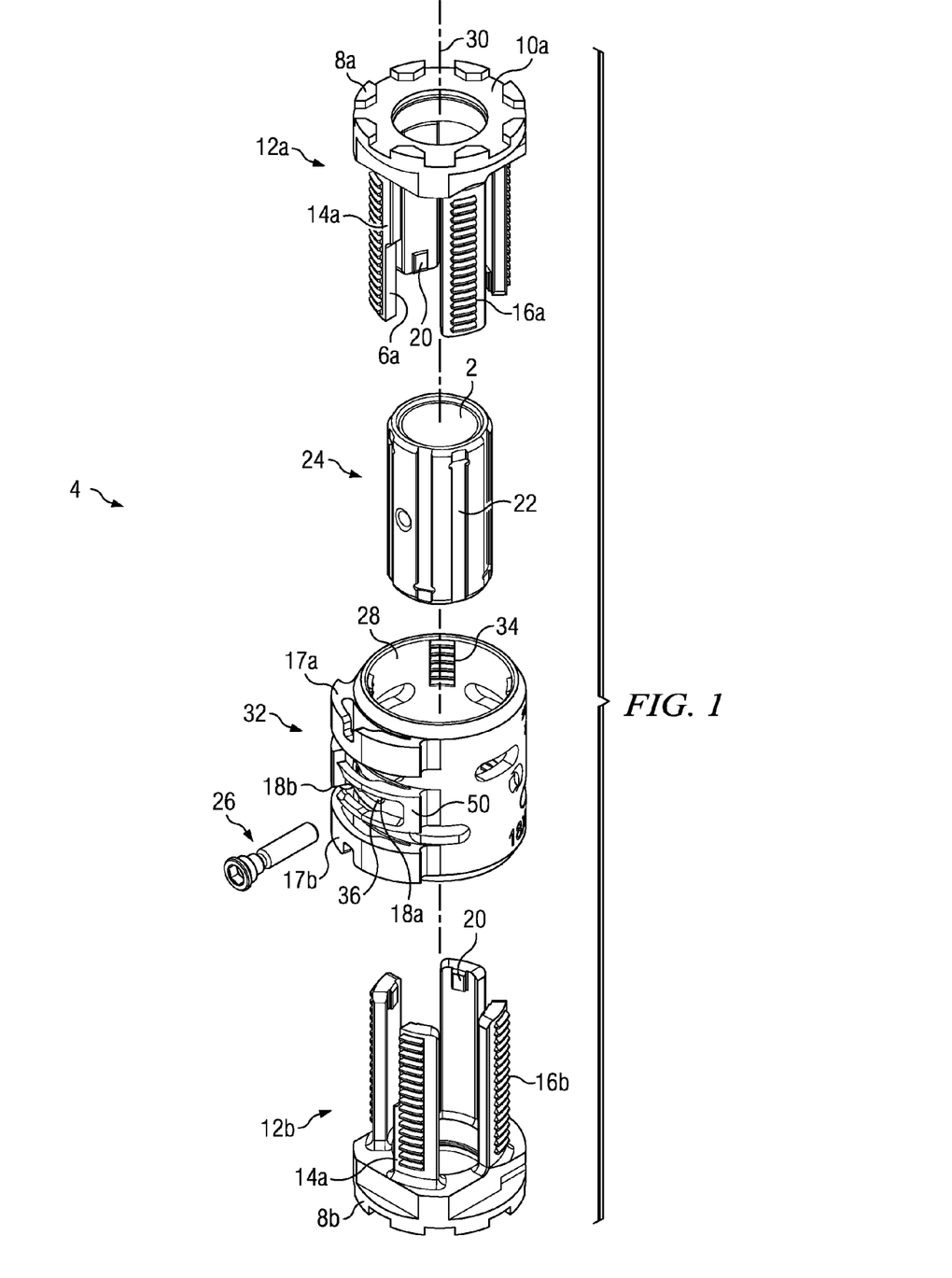
FIG. 1 is an exploded view of an expandable support device according to one embodiment of the present disclosure.

FIG. 1 is an exploded view of an expandable support device 4 according to one embodiment of the present disclosure. One or more adjacent vertebral bodies 66 and one or both surrounding vertebral discs—as well as the vertebral discs between the removed vertebral bodies 66—can be removed from a target site. The expandable support device 4 can then be inserted into the target site and expanded to provide mechanical support in the spine 62 between the remaining vertebral bodies 66. The embodiment of the expandable support device illustrated in FIG. 1 is described in U.S. application Ser. No. 12/684,825 to Greenhalgh et al. and is hereby incorporated by reference in its entirety. It should be appreciated that many features disclosed in this application, including, but not limited to posterior insertion instrument 100, are not taught, suggested, or disclosed in U.S. application Ser. No. 12/684,825.

The expandable support device 4 can have an outer cylinder 32, an inner cylinder 24, a first end piece 12a and a second end piece 12b. The expandable support device 4 can be expanded and can mechanically, structurally support orthopedic structures in vivo, whether those orthopedic structures are the aforementioned vertebrae 64, other bones, or soft tissue.

The first end piece 12a and second end piece 12b can be substantially identical or different from each other in shape and structure. The first end piece 12a can be symmetric or a mirror-image of the second end piece 12b. The first 12a and second 12b end pieces can have terminal first 8a and second 8b ends, respectively. The ends can have end faces. The end faces can be smooth or textured. The end faces can be textured with knurling, spikes, ridges, bumps, or combinations thereof. A first end face 10a can be textured with a first texture and the second end face 10b can be smooth or textured with a second texture that can be the same or different from the first texture. The end faces can be configured to abut or dig into adjacent tissue (e.g., bone) during implantation. Either or both end faces can be made from or lined with a matrix to encourage tissue ingrowth into the end face.

The end pieces can have one or more end piece extensions or legs extending from the respective end faces longitudinally inward toward the longitudinal center of the expandable support device 4. The extensions can have one or more radially outward-facing end piece teeth. The end piece teeth can be configured in a longitudinal column parallel with the longitudinal axis 30 on each extension. The end piece teeth can be oriented in transverse planes, perpendicular to the longitudinal axis 30 and along an angular path at a constant radius with respect to the longitudinal axis 30. Each end piece tooth can extend across half (as shown) or substantially all of the radially outer surface of the extension.

One, two or all of the extensions can have radially inwardly-facing guide pegs 20. The guide pegs 20 can be at or near the longitudinally terminal ends of the extensions away from the respective end face.

End piece slots 6 can be formed by open areas between the extensions.

The inner cylinder 24 can form a center channel 2. The inner cylinder 24 can have longitudinal guide slots 22 on the radially outer surface of the inner cylinder 24. The guide slots 22 can be configured to interface with, or receive, the guide pegs 20. The guide slots 22 can be configured to longitudinally slidably attach to the guide pegs 20. The guide slots 22 can constrain the guide pegs 20 to prevent the end pieces (and guide pegs 20) from rotating with respect to the inner cylinder 24.

During use, filler can be inserted through the end piece slots 6 and into the center channel 2 before during or after insertion of the device 4 into the target site and/or extension of the device 4. The filler can be chunks of morselized bone, powder (e.g., BMP), liquid (e.g., PMMA), all of which are listed and for which examples are given below, or combinations thereof.

The inner cylinder 24 can have one or more a radially outwardly extending lock screws 26. The lock screws 26 can have heads at the radially outermost terminal end of the lock screw 26. The heads of the lock screws 26 can be wider than the shafts of the lock screws 26. The lock screws 26 can be spring-loaded, clips, or combinations thereof. As used herein, screw 26 can refer to any suitable type of fastener with its head and body configured in any suitable way in use with the present application.

The outer radius of the inner cylinder 24 can be smaller than the inner radius of the end piece extensions.

The outer cylinder 32 can have a screw slot 36 configured to slidably receive the lock screw 26. The outer cylinder 32 can have an inner radius that is larger than the outer radius of the end piece extensions.

The screw slot 36 can have a first stop 18a at a first terminal end of the screw slot 36. The screw slot 36 can have a second stop 18b at a second terminal end of the screw slot 36. The first 18a and second 18b stops can abut and interference fit against the lock screw 26 shaft when the outer cylinder 32 and inner cylinder 24 are rotated with respect to each other to the respective limits of rotation. The angular limit of rotation of the outer cylinder 32 with respect to the inner cylinder 24 can be defined by and identical to the screw slot angle. The screw slot angle can be an angle measured from the longitudinal axis 30 between the first stop 18a and the second stop 18b.

The outer cylinder 32 can have columns of radially inwardly-facing outer cylinder teeth 34. The outer cylinder teeth 34 can be configured in longitudinal columns parallel with the longitudinal axis 30. The outer cylinder teeth 34 can be oriented in transverse planes, perpendicular to the longitudinal axis 30 and along an angular path at a constant radius with respect to the longitudinal axis 30. The outer cylinder teeth 34 can have be spaced so the toothless areas of the inner surface of the outer cylinder 32 can define a locking gap 28 between adjacent columns of outer cylinder teeth 34. The locking gaps 28 can be are at least as wide as the width of the end piece teeth. The end piece teeth can be narrower than the outer cylinder teeth 34.

The end piece teeth can slide between the outer cylinder teeth 34 when the outer cylinder 32 is rotated appropriately with respect to the end pieces. When the guide pegs 20 are engaged in the guide slots 22, the end pieces and inner cylinder 24 can rotate as a single unit with respect to the outer cylinder 32. The screw slot 36 and screw can be configured so that the end piece teeth do not longitudinally interfere with the outer cylinder teeth 34 (i.e., an unlocked configuration) when the screw is at one end of the screw slot 36. For example, this unlocked configuration can permit the end pieces to longitudinally translate (i.e., expand and contract) with respect to the outer cylinder 32 and the opposite end piece.

The screw slot 36 and screw 26 can be configured so that the end piece teeth longitudinally interfere with the outer cylinder teeth 34 (i.e., a locked configuration) when the screw is at the opposite end of the screw slot 36 from the unlocked configuration. For example, this locked configuration can create an interference fit between the end piece teeth and the outer cylinder teeth 34, for example, substantially preventing the end pieces from longitudinally translating (i.e., expand and contract) with respect to the outer cylinder 32 and the opposite end piece.

The outer cylinder 32 can have a lock screw 26, such as a hex screw. The lock screw 26 can traverse the wall of the outer cylinder 32. The lock screw 26 can be configured to be radially translatable with respect to the outer cylinder 32 when screwed through the outer cylinder 32 wall. The lock screw 26 can be screwed toward the longitudinal center of the outer cylinder 32 to fix the outer cylinder 32 to the first end piece 12a, second end piece 12b, inner cylinder 24 or combinations thereof, for example, for additional locking.

Lock screw 26 can be tightened (e.g., screwed toward the center of the outer cylinder 32) to press the lock screw 26 against the first 12a and/or second 12b end piece and/or inner cylinder 24 to produce a frictional resistance. The lock screw 26 can deform the first end piece 12a and/or second end piece 12b, pressing the first 12a and/or second 12b end pieces (e.g., the respective extensions) into the inner cylinder 24, creating a frictional force between the inner cylinder 24 and the first 12a and/or second 12b end pieces 12b.

Lock screw 26 can be unscrewed away from the longitudinal center of the outer cylinder 32, releasing the first end piece 12a and second end piece 12b from being fixed to the outer cylinder 32. The first end piece 12a and/or second end piece 12b can be longitudinally translated or extended away from the outer cylinder 32. The guide pegs 20 can slide within the guide slots 22, restricting the end pieces from rotating with respect to the inner cylinder 24.

The device 4 can have snaps or threads on the end pieces, for example to engage the vertebral body 66 end plates. The end pieces can be smooth or rough (e.g., with texturing or teeth). The end pieces can have angles relative to the longitudinal axis 30 of the cylinders and/or the other end piece. The devices end pieces can have teeth or angle without the snap on pieces.

The end pieces can have four extensions, as shown, or more or less extensions. The end piece teeth can be next to each other, as shown, or can be in the center of each column. The ratio of the outer surface area of the end piece extensions covered by teeth to non-tooth surface area can be about 50%.

Figures 2A, 2B:
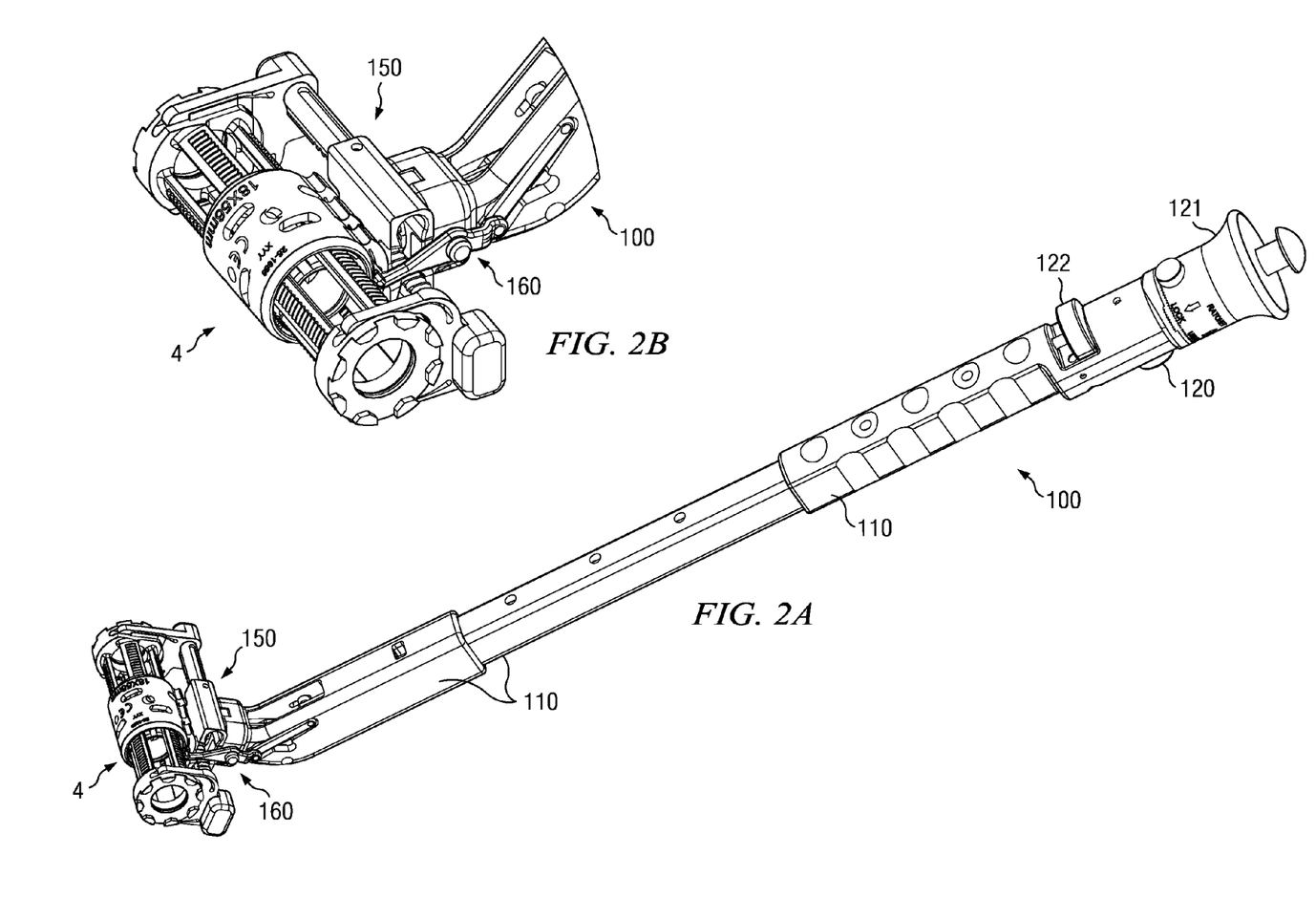
FIG. 2A is a perspective view of the exterior of an insertion instrument secured to an expandable support device according to one embodiment of the present disclosure.
FIG. 2B is a blown-up view of the exterior of an insertion instrument secured to an expandable support device according to one embodiment of the present disclosure.
Figures 4A, 4B:
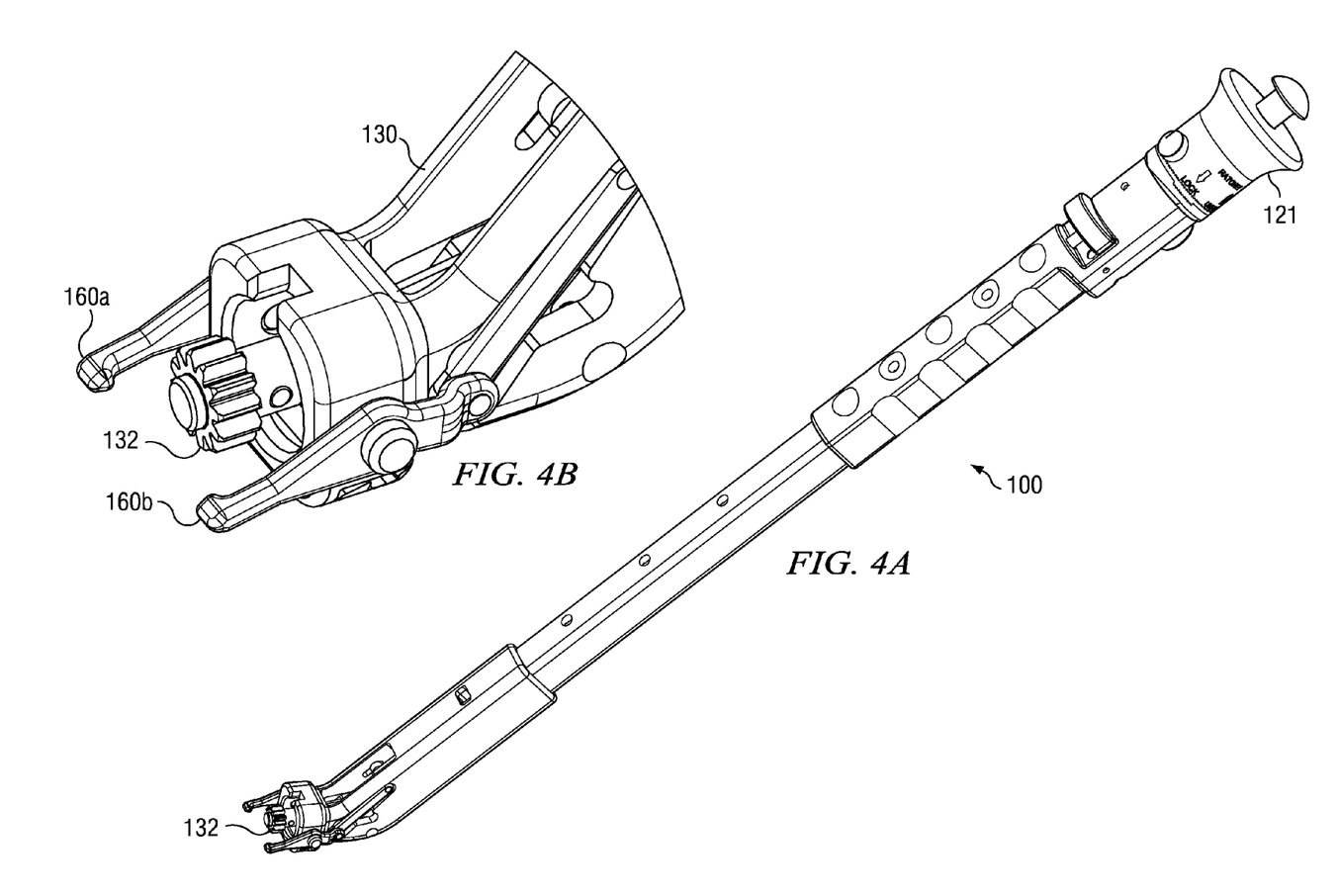
FIG. 4A is a perspective view of an insertion instrument configured with a gear driver shaft according to one embodiment of the present disclosure.
FIG. 4B is a blown-up view of an insertion instrument configured with a gear driver shaft according to one embodiment of the present disclosure.

FIG. 2A is a perspective view of the exterior of an insertion instrument 100 secured to an expandable support device 4 according to one embodiment of the present disclosure. FIG. 2B is a blown-up view of the exterior of an insertion instrument secured to an expandable support device according to one embodiment of the present disclosure. Insertion instrument 100 includes a hollow body 110 having one or more cannulations, which may house one or more tools within cannulations in body 110. Insertion instrument 100 also includes a release button 120, which allows for the one or more tools within cannulated body 110 to be removed or replaced with other tools. Insertion instrument 100 also includes a rotation lever 122, which actuates linkages and/or levers 160 in a particular direction, which causes outer cylinder 32 to rotate, which is explained in more detail below in FIG. 8. Insertion instrument 100 may be secured to an attachment device 150, which may attach to expandable support device 4. Insertion instrument 100 may include a ratchet handle 121, which may cause gear shaft drive 130 and gear device 132 to rotate, as illustrated in FIGS. 4A and 4B.

Figure 3:
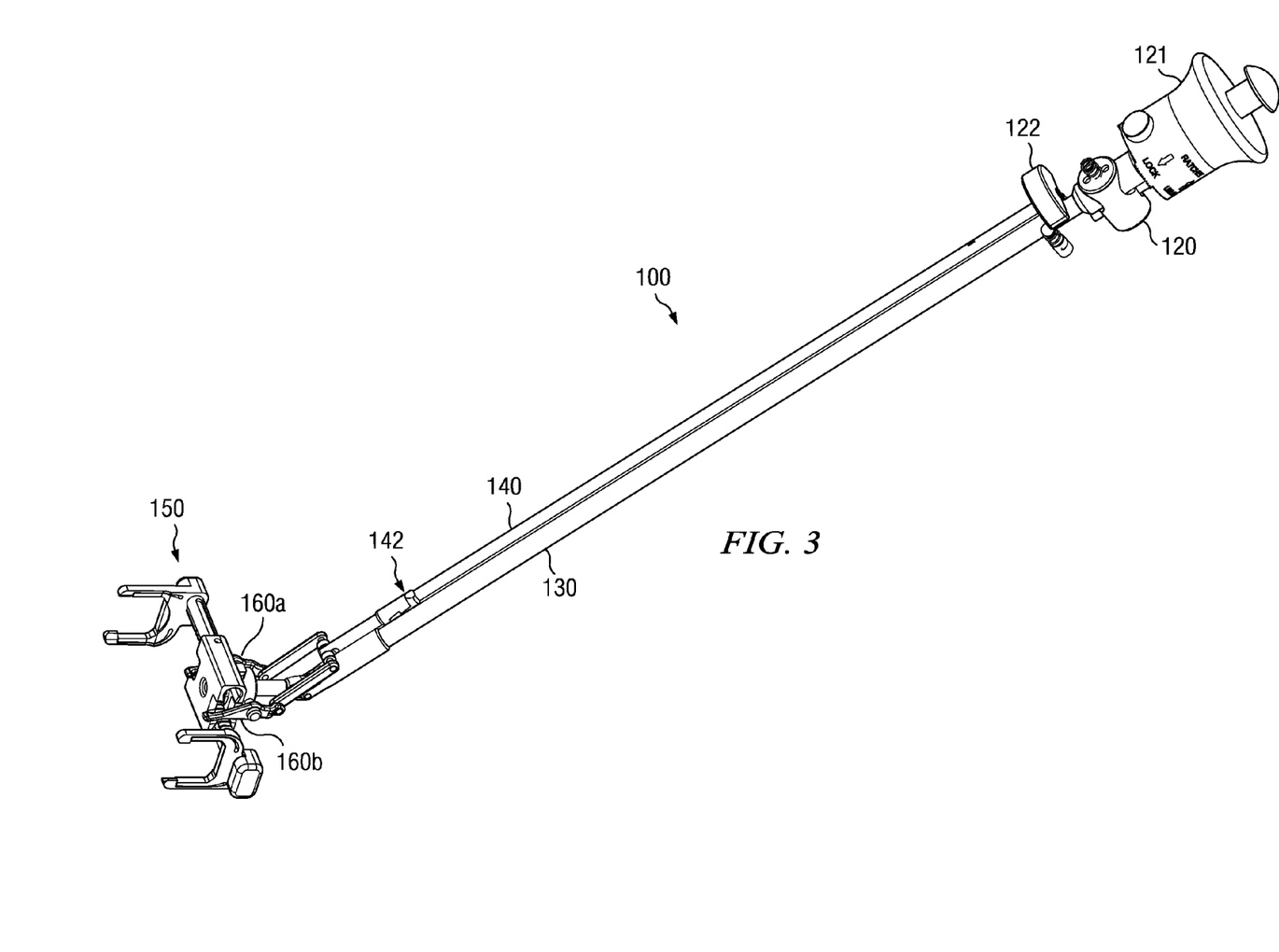
FIG. 3 is a perspective view of the interior of an insertion instrument according to one embodiment of the present disclosure.

FIG. 3 is a perspective view of the interior of an insertion instrument 100 according to one embodiment of the present disclosure. FIG. 3 is an illustration where cannulated body 110 is not illustrated. Cannulated body 110 may house one or more tools, including, but not limited to, gear driver shaft 130, screw driver shaft 136, and/or linkage shaft 140, etc. Although the illustrated embodiment of insertion instrument 100 includes a gear driver shaft 130 and linkage shaft 140, any number of shafts or tools may be used to carry out the teachings in this disclosure.

Insertion instrument 100 may also include a release button 120, which allows for the one or more tools within cannulated body 110 to be removed or replaced with other tools. For example, gear driver shaft 130 may be removed and replaced by screw driver shaft 136 or any other tool. Similarly, screw driver shaft 136 may be removed and replaced by gear driver shaft 130 or any other tool.

Insertion instrument 100 may also include a rotation lever 122, which actuates linkage shaft 140, which actuates linkages 160 in a particular direction, which causes outer cylinder 32 to rotate, which is explained in more detail below in FIG. 8.

Linkage shaft 140 may include a disconnect feature 142, which allows for the removal of the major portion of linkage shaft 140. In some embodiments, disconnect feature 142 may be spring loaded to allow the engagement and disengagement of portions of linkage shaft 140. Thus, insertion instrument 100 may capable of removing all interior tools within its cannulated body 110, which may allow for X-Rays to appear more visible since tools 130, 136, 140 will not be scanned.

Gear driver shaft 130 and screw driver shaft 136 may be a universal joint which allows gear driver shaft 130 to bend in one or more directions. Although the illustrated embodiment includes a bend near the end of gear driver shaft 130, the bend may be anywhere on gear driver shaft 130 or screw driver shaft 136, and there may be one or more additional bends in gear driver shaft 130 or screw driver shaft 136. Gear driver shaft 130 is explained in more detail below in FIGS. 4A and 4B. Screw driver shaft 136 is described in more detail below in FIGS. 5A and 5B.

FIG. 4A is a perspective view of an insertion instrument 100 configured with a gear driver shaft 130 according to one embodiment of the present disclosure. FIG. 4B is a blown-up view of an insertion instrument 100 configured with a gear driver shaft 130 according to one embodiment of the present disclosure. Gear driver shaft 130 may include a guiding device 133 and gear device 132. Insertion instrument 100 may include a ratchet handle 121, which may cause gear shaft drive 130 and gear device 132 to rotate.

Figure 7:
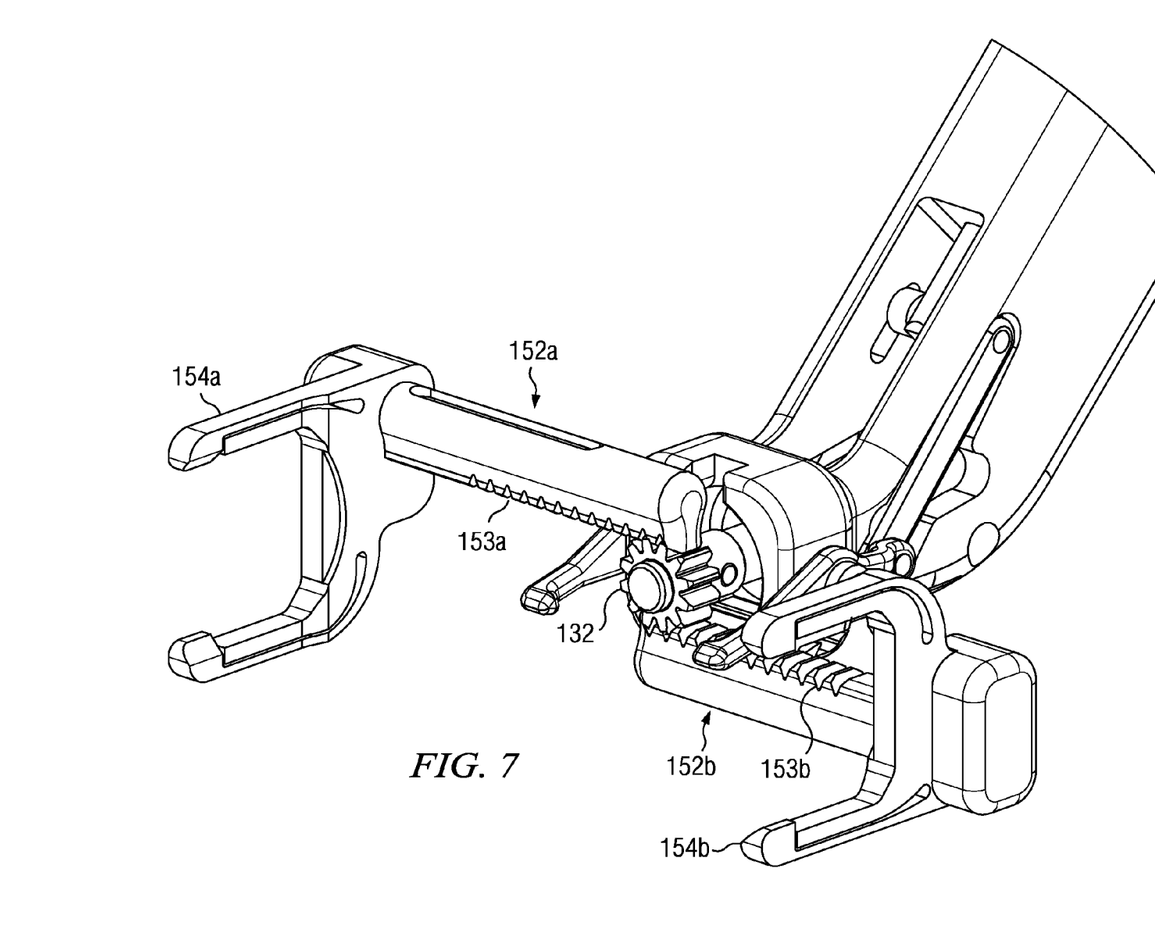
FIG. 7 is a perspective view of a gear driver shaft interacting with gears of a gear driver shaft according to one embodiment of the present disclosure.

Gear device 132 may be any type of device which can interact with expansion device to cause extendable legs 12a, 12b to expand or contract, which is explained below in more detail in FIG. 7.

Figure 6:
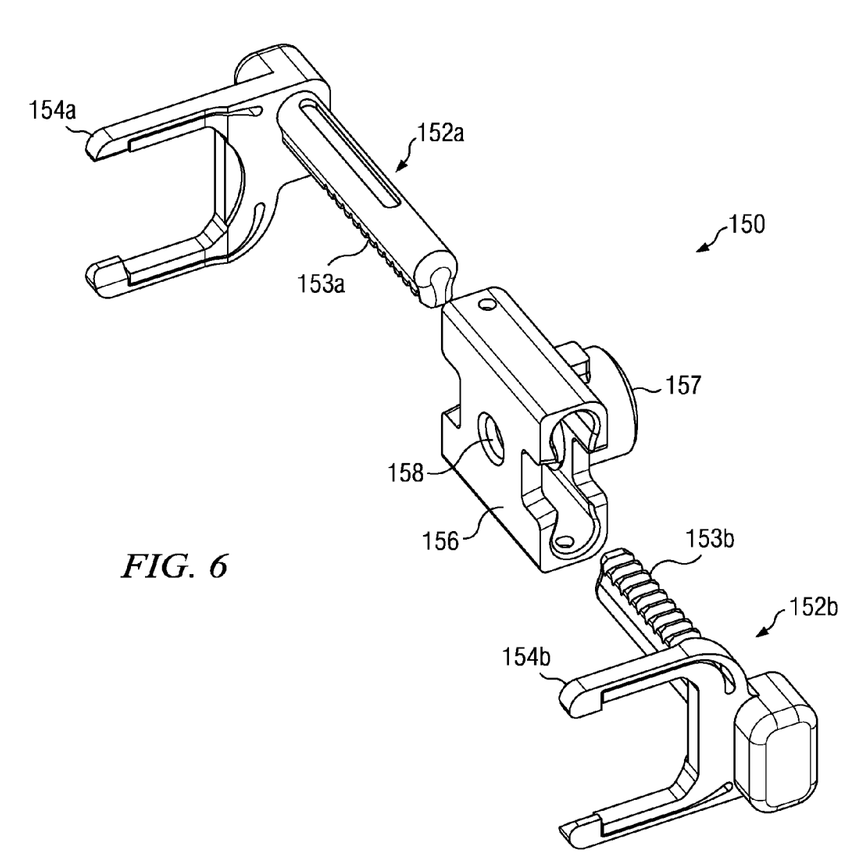
FIG. 6 is an exploded view of an attachment device according to one embodiment of the present disclosure.

Guiding device 133 may be configured, such that it fits within opening 157 of attachment device 150, as illustrated in FIG. 6.

Figures 5A, 5B:
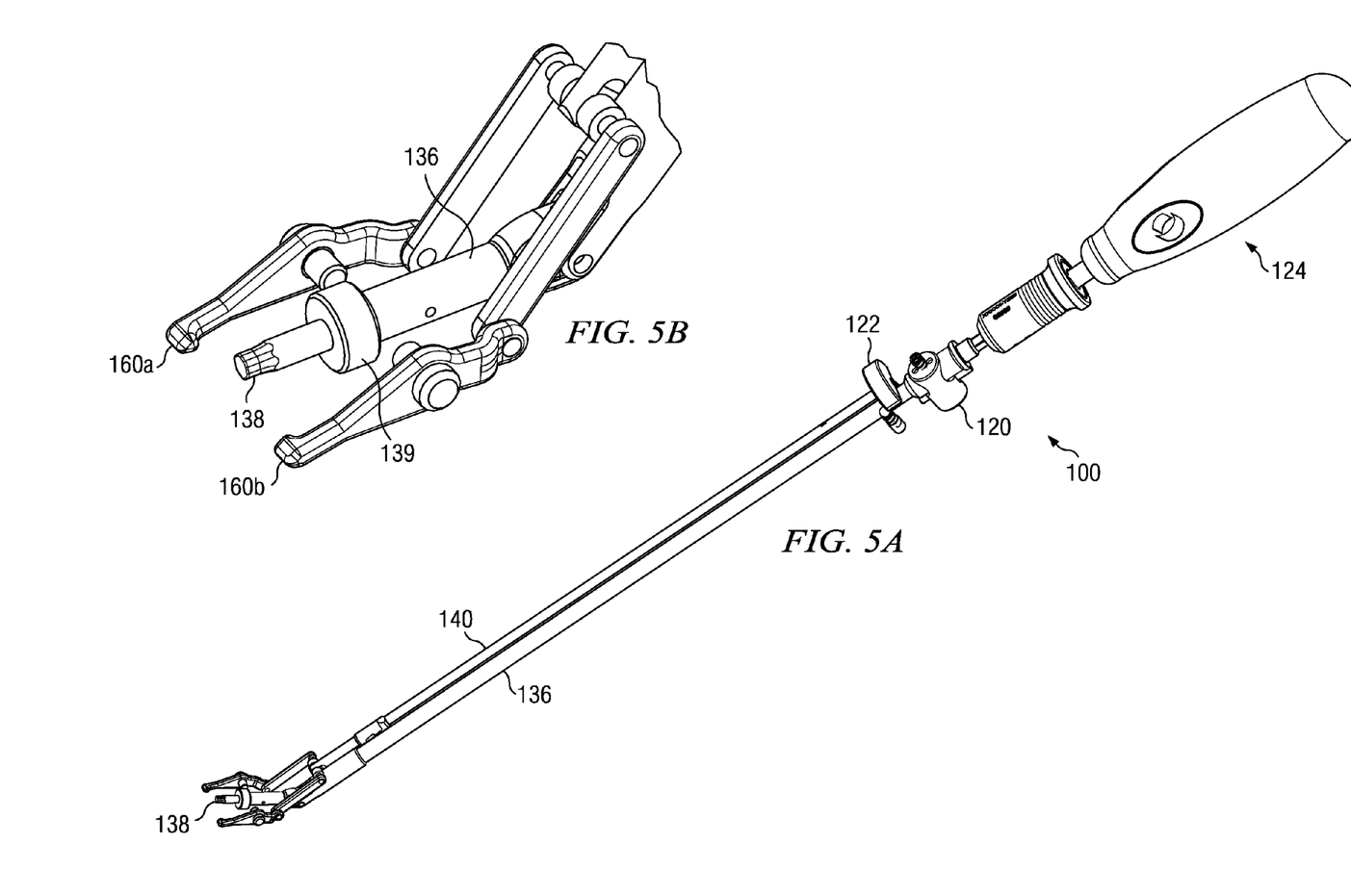
FIG. 5A is a perspective view of an insertion instrument configured with a screw driver shaft according to one embodiment of the present disclosure.
FIG. 5B is a blown-up view of an insertion instrument configured with a screw driver shaft according to one embodiment of the present disclosure.

FIG. 5A is a perspective view of an insertion instrument 100 configured with a screw driver shaft 136 according to one embodiment of the present disclosure. FIG. 5B is a blown-up view of an insertion instrument 100 configured with a screw driver shaft 136 according to one embodiment of the present disclosure. Screw driver shaft 136 may include a guiding device 139 and screw driver 138.

Screw driver device 138 may be any type of device which can interact with any type of fastener 26, including, but not limited to hex screw, square screw, flat screw, Phillips screw, torx screw, etc. Screw driver device 138 may be able to exert force on fastener 26, such that fastener is driven into expandable support device 4, which may cause a locked position and prevent rotation of the outer cylinder 32 with extendable legs 12a, 12b to expand or contract, which is explained below in more detail in FIG. 7. Insertion instrument 100 may include a screw driver handle 121, which may allow screw driver shaft 138 and screw driver device 138 to drive fastener 26 into expandable support device 4.

Guiding device 139 may be configured, such that it fits within opening 157 of attachment device 150, as illustrated in FIG. 6.

FIG. 6 is an exploded view of an attachment device 150 according to one embodiment of the present disclosure. FIG. 7 is a perspective view of a gear driver shaft interacting with gears of a gear driver shaft 130 according to one embodiment of the present disclosure. Attachment device 150 may include a base 156, which may include a guiding opening 157 and a fastener opening 158. Attachment device 150 may also include extendable holders 152a, 152b to hold, extend, and contract extendable legs 12a, 12b. Extendable holders 152a, 152b may move in either direction through any means necessary, including, but not limited to a rack and pinion mechanism, a bevel gear, a worm gear, etc. In the illustrated embodiment, teeth 153a, 153b engage gear device 132, such that extendable holders 152a, 152b extend or collapse according to the rotation of gear device 132.

Extendable holders 152a, 152b may attach to expandable support device 4 by any suitable mechanism. In the illustrated embodiment, extendable holders 152a, 152b may attach to extendable legs 12a, 12b with spring clamps 154a, 154b. Spring clamps 154a, 154b may flex outward until properly engaged with a portion of extendable legs 12a, 12b.

Figure 8:
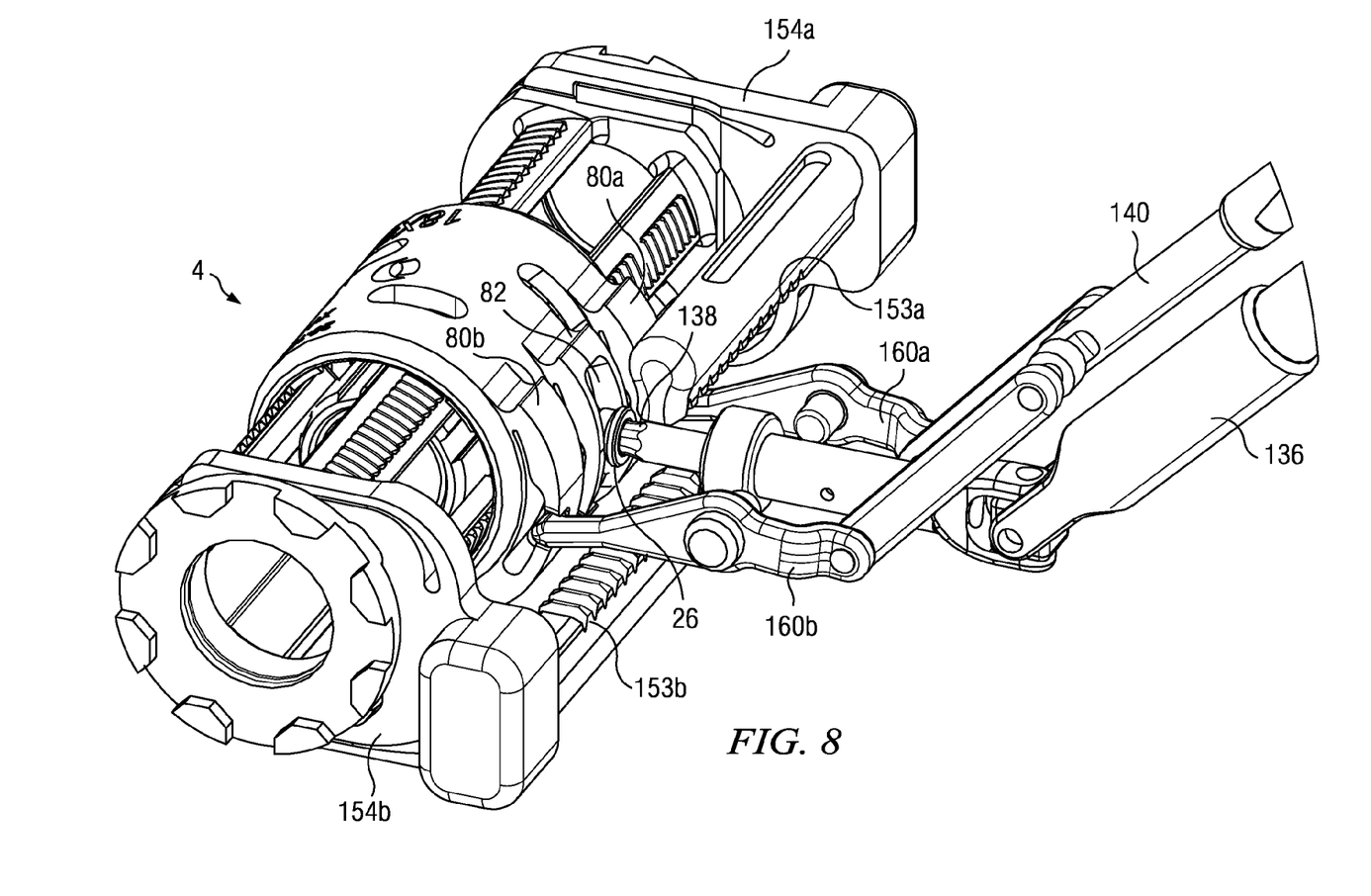
FIG. 8 is a perspective view of an insertion instrument secured with a screw driver shaft secured to an expandable support device according to one embodiment of the present disclosure.

FIG. 8 is a perspective view of an insertion instrument 100 secured with a screw driver shaft 136 secured to an expandable support device 4 according to one embodiment of the present disclosure. Expandable support device 4 may include linkage capture devices 80a, 80b to capture linkages 160a, 160b, and screw capture device 82 to capture screw 26.

Figures 9A, 9B:
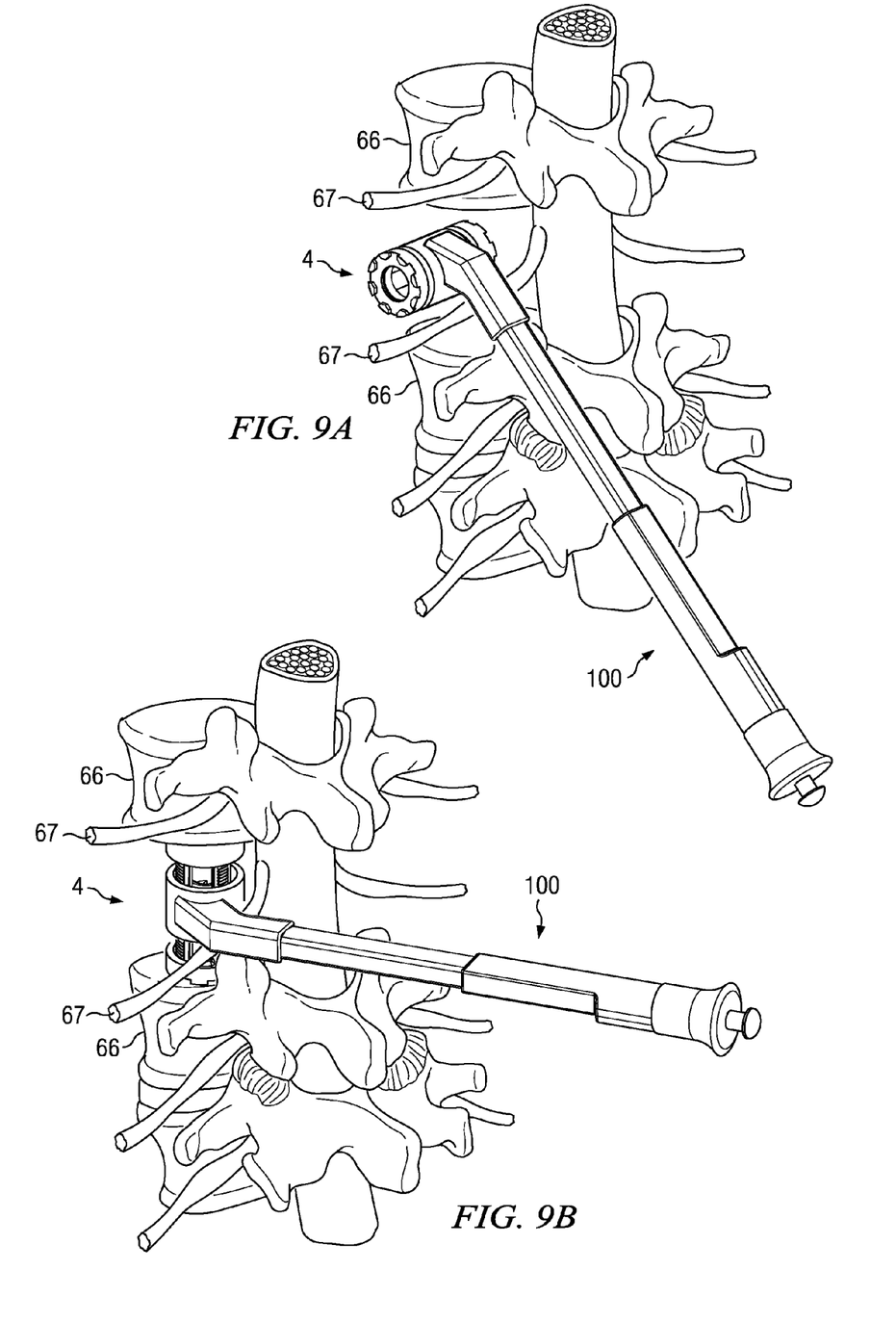
FIG. 9A is a posterior view of an insertion instrument inserting an expandable support device within vertebral bodies of a spine according to one embodiment of the present disclosure.
FIG. 9B is a lateral view of an insertion instrument inserting an expandable support device in its extracted configuration within vertebral bodies of a spine according to one embodiment of the present disclosure.

In operation, a physician may create an incision in posterior (back) of patient. The incision may only need to be as large as the width of the compressed configuration of expandable support device 4. In some embodiments, the incision may be less than twenty millimeters, which is a very small incision relative to the typical incisions needed to insert or remove an vertebral body replacement. As illustrated in FIGS. 9A and 9B, insertion instrument 100 may be adapted to insert expandable support device 4 between nerve roots 67. After expandable support device 4 has made it past nerve roots 67, insertion instrument may be turned approximately ninety degrees to place expandable support device 4 in a longitudinal position between vertebral bodies 66. Although insertion instrument 100 is illustrated as having an angled distal tip, insertion instrument 100 may configured in any shape to carry out the teachings of this disclosure. The device longitudinal axis 70 of the expandable support device 4 can be substantially parallel with the spinal longitudinal axis 72. The device can be implanted in the spine for partial or complete corpectomy.

After the compressed configuration of expandable support device 4 is placed longitudinally between vertebral bodies 66, physician may interact with ratchet handle 121, which may cause gear shaft drive 130 and gear device 132 to engage and rotate about teeth 153a, 153b of attachment device 150. As the gear device 132 rotates, extendable holders 152a, 152b may extend or collapse extendable legs 12a, 12b of expandable support device 4 according to the rotation of gear device 132. Accordingly, insertion instrument 100 is capable of expanding or contracting expandable support device to a desired position.

After the expandable support device 4 has been expanded to the desired position, insertion instrument may be used to rotate outer cylinder 32 to lock this desired position (or height) in place. A first or unrotated position may be referred to as an unlocked position because the outer cylinder teeth 34 may not be aligned with end piece teeth 16a, 16b, and thus the extendable legs 12a, 12b are unlocked to expand or contract. A second or rotated position may be referred to as a locked position because the outer cylinder teeth 34 may be aligned with end piece teeth 16a, 16b, and thus the extendable legs 12a, 12b are locked into that particular configuration. Accordingly, unlocked position and locked position may be obtained by rotating the outer cylinder 32. Physician may maneuver a rotation lever 122 on insertion instrument 100, which may actuate linkage shaft 140 and linkages 160a, 160b in a particular direction, which may cause outer cylinder 32 to rotate into a locked or unlocked position. Linkages 160a, 160b may be secured to outer cylinder 32 by linkage capture devices 80a, 80b.

After insertion instrument 100 has rotated outer cylinder of expandable support device 4 and locked the height into place, physician may desire to insert fastener 26 to secure this rotated configuration in place. Physician may interact with release button 120, which allows for removal of gear driver shaft 130 and the insertion of screw driver shaft 136. After maneuvering guiding device 139 of screw driver shaft 136 into opening 157 of attachment device 150, Physician may maneuver screw driver handle 121, which may allow screw driver shaft 138 and screw driver device 138 to drive fastener 26 into screw capture device 82 of expandable support device 4 to capture screw 26. Capture device 82 may be used to effectively capture screw 26. Capture device 82 may be designed in any suitable manner to effectively capture screw 26 in the locked position. For example, the width between arms of capture device may be dependent on the width of screw 26. In other embodiments, capture device 82 may be a boring adapted to receive screw 26. In some embodiments, any suitable retaining mechanism may be used to prevent screw 26 from backing out. Accordingly, retaining mechanism may prevent screw 26 from backing out even if device 4, or screw 26 would typically become loosened after being subject to shock, vibration, or any other type of disturbance.

After insertion instrument has locked the rotated configuration of expandable support device 4, physician may desire to disengage insertion instrument 100 and attachment device 150 from expandable support device 4. Any suitable mechanism may be used to disengage insertion instrument. In one embodiment, physician may replace screw driver shaft 138 with gear driver shaft 130. Physician may interact with ratchet handle 121, which may cause gear shaft drive 130 and gear device 132 to engage and rotate about teeth 153*a*, 153*b* of attachment device 150. As the gear device 132 rotates, extendable holders 152*a*, 152*b* may collapse from the outer diameter end pieces 8*a*, 8*b* of extendable legs 12*a*, 12*b* and disengage the extendable legs 12*a*, 12*b*. Physician may continue to compress extendable holders 152*a*, 152*b* to their compressed configuration before removing insertion instrument and attachment device 150. Next, physician may remove insertion instrument 100 and attachment device 150 from the posterior incision after successfully placing, extending, rotating, and locking expandable support device 4 with insertion instrument 100.

FIG. 9A is a posterior view of an insertion instrument inserting an expandable support device 4 within vertebral bodies 66 of a spine according to one embodiment of the present disclosure.

FIG. 9B is a lateral view of an insertion instrument inserting an expandable support device 4 in its extracted configuration within vertebral bodies 66 of a spine according to one embodiment of the present disclosure.

Although the illustrated embodiments describe rotating outer cylinder 32 and locking the configuration (height) of expandable support device 4 into place using link shaft 140 and linkages 160*a*, 160*b*, any other suitable mechanism may be used. For example, a tool with a hook or grasping device may be used in insertion instrument 100 to rotate outer cylinder 32 to its desired position. The insertion instrument 100 may be configured in any suitable manner with any suitable tools to achieve the teachings in this disclosure. The configuration of insertion instrument 100 and the tools used as part of insertion instrument 100 may depend on the configuration of expandable support device 4.

The device 4 can be partially or substantially completely filled with a filler through the slots between the end piece extensions and/or through the ports formed at the longitudinal ends of the device 4. The device 4 can be filled by the filler before and/or after deployment into the target site between vertebral bodies.

A physician can adjust the length of the device 4 after inspecting the target site between vertebral bodies. More than one device 4 can be placed longitudinal end-to-end with other devices 4, for example to stack the devices as desired.

The expandable support device 4 can be deployed in a vessel, in or around an aneurysm, across a valve, or combinations thereof. The expandable support device 4 can be deployed permanently and/or used as a removable tool to expand or clear a lumen and/or repair valve leaflets.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

If any device in this disclosure is machined onto device 4, the material should preferably be made of a material that can conduct electricity. Otherwise, any or all elements of the expandable support devices 4, and/or deployment tool, and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E.I. Du Pont de Nemours and Company, Wilmington, Del.), poly ester amide (PEA), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

Any or all elements of the expandable support devices 4, and/or deployment tool, and/or other devices or apparatuses described herein, can be, have, and/or be completely or partially coated with agents and/or a matrix a matrix for cell ingrowth or used with a fabric, for example a covering (not shown) that acts as a matrix for cell ingrowth. The matrix and/or fabric can be, for example, polyester (e.g., DACRON® from E.I. Du Pont de Nemours and Company, Wilmington, Del.), poly ester amide (PEA), polypropylene, PTFE, ePTFE, nylon, extruded collagen, silicone, any other material disclosed herein, or combinations thereof.

The expandable support devices 4 and/or insertion instrument, and/or elements of the expandable support devices 4, and/or insertion instrument, and/or other devices or apparatuses described herein and/or the fabric can be filled, coated, layered and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin E.sub.2 Synthesis in Abdominal Aortic Aneurysms, Circulation, Jul. 6, 1999, 48-54; Tambiah et al, Provocation of Experimental Aortic Inflammation Mediators and Chlamydia Pneumoniae, Brit. J. Surgery 88 (7), 935-940; Franklin et al, Uptake of Tetracycline by Aortic Aneurysm Wall and Its Effect on Inflammation and Proteolysis, Brit. J. Surgery 86 (6), 771-775; Xu et al, Sp1 Increases Expression of Cyclooxygenase-2 in Hypoxic Vascular Endothelium, J. Biological Chemistry 275 (32) 24583-24589; and Pyo et al, Targeted Gene Disruption of Matrix Metalloproteinase-9 (Gelatinase B) Suppresses Development of Experimental Abdominal Aortic Aneurysms, J. Clinical Investigation 105 (11), 1641-1649 which are all incorporated by reference in their entireties.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. An insertion instrument for inserting an expandable support device, the insertion instrument comprising:
 a hollow body comprising a cannulation operable to receive a removable gear device or a removable screw driver device;
 an actuator device; and
 a release button;
 wherein the removable gear device is configurable to cause a first longitudinally extending member of expandable support device to longitudinally extend in a direction away from the center of the expandable support device;
 wherein the actuator device is operable to rotate a component of an expandable support device to a rotated position, wherein the rotation to the rotated position of the expandable support device causes the first longitudinally extending member of the expandable support device to be longitudinally fixed;
 wherein the removable screw driver device is configurable to engage a fastener on the expandable support device to lock the expandable support device into place in the rotated position;
 wherein the release button is operable to allow for removal of the removable gear device from the cannulation of the hollow body and insertion of the removable screw driver device into the cannulation of the hollow body.

2. The insertion instrument of claim 1, wherein the removable gear device is configurable to cause a second longitudinally extending member of expandable support device to longitudinally extend in a direction opposite from the first longitudinally extending member.

3. The insertion instrument of claim 1, wherein the removable gear device comprises a gear shaft and a gear, and wherein the removable gear device engages with an attachment device comprising a device secured to the first longitudinally extending member of the expandable support device, wherein the device secured to the first longitudinally extending member comprises teeth, which engage with the gear.

4. The insertion instrument of claim 1, wherein the gear device is used with another device secured to the first longitudinally extending member to form a rack and pinion system for extending the first longitudinally extending member in either direct along the longitudinal axis.

5. The insertion instrument of claim 1, wherein the fastener is a screw.

6. The insertion instrument of claim 5, wherein the screw is a hex screw.

7. The insertion instrument of claim 1, wherein the actuator device comprises a link shaft and a linkage secured to a component integral with a rotatable component of the expandable support device.

8. The insertion instrument of claim 1, wherein the removable gear device can be replaced by the removable screw device.

9. The insertion instrument of claim 1, wherein the body of the insertion instrument has an angular distal tip to allow insertion instrument to maneuver between nerve between nerve roots and behind the spinal cord to position the expandable support between vertebral bodies.

10. The insertion instrument of claim 1, wherein the insertion instrument is inserted in an incision on a posterior of patient.

11. A method for inserting an expandable support device with an insertion instrument, the method comprising:
 securing an expandable support device to an insertion instrument, wherein the insertion instrument comprises a removable gear device and an actuator device;
 positioning the expandable support device in a longitudinal position between vertebral bodies;
 interacting with the removable gear device to cause a first longitudinally extending member of the expandable support device to longitudinally extend in a direction away from the center of the expandable support device;
 interacting with the actuator device to rotate a component of the expandable support device to a rotated position, wherein the rotation to the rotated position of the expandable support device causes the first longitudinally extending member of the expandable support device to be longitudinally fixed;
 interacting with a release button for removing the removable gear device from a cannulation of a hollow body of the insertion instrument;
 inserting a removable screw driver device into the cannulation of the hollow body of the insertion instrument; and interacting with the removable screw driver device to engage a fastener on the expandable support device to lock the rotated position into place.

12. The method of claim 11, wherein the removable gear device is configurable to cause a second longitudinally extending member of expandable support device to longitudinally extend in a direction opposite from the first longitudinally extending member.

13. The method of claim 11, wherein the removable gear device comprises a gear shaft and a gear, and wherein the removable gear device engages with an attachment device comprising a device secured to the first longitudinally extending member of the expandable support device, wherein the device secured to the first longitudinally extending member comprises teeth, which engage with the gear.

14. The method of claim 11, wherein the gear device is used with another device secured to the first longitudinally extending member to form a rack and pinion system for extending the first longitudinally extending member in either direct along the longitudinal axis.

15. The method of claim 11, wherein the fastener is a screw.

16. The method of claim 15, wherein the screw is a hex screw.

17. The method of claim 11, wherein the actuator device comprises a link shaft and a linkage secured to a component integral with a rotatable component of the expandable support device.

18. The method of claim 11, wherein the method further comprises:
removing the removable screw driver device from the cannulation of the insertion instrument;
inserting the removable gear device into the cannulation of the insertion instrument; and
interacting with the removable gear device to disengage the insertion device from the expandable support device.

19. The method of claim 11, wherein the body of the insertion instrument has an angular distal tip to allow the insertion instrument to maneuver between nerve between nerve roots and behind the spinal cord to position the expandable support between vertebral bodies.

20. The method of claim 11, wherein the insertion instrument is inserted in an incision on a posterior of patient.

* * * * *